United States Patent [19]
Narayanan

[11] Patent Number: 5,266,590
[45] Date of Patent: Nov. 30, 1993

[54] COLD STABILIZATION OF AQUEOUS MICROEMULSIONS OF A WATER-INSOLUBLE AGRICULTURALLY ACTIVE COMPOUND

[75] Inventor: Kolazi S. Narayanan, Palisades Park, N.J.

[73] Assignee: ISP Investments Inc., Wilmington, Del.

[21] Appl. No.: 978,833

[22] Filed: Nov. 19, 1992

Related U.S. Application Data

[63] Continuation-in-part of Ser. No. 777,032, Oct. 16, 1991, abandoned, which is a continuation-in-part of Ser. No. 654,250, Feb. 12, 1991, abandoned, which is a continuation-in-part of Ser. No. 546,014, Jun. 28, 1990, Pat. No. 5,165,666, which is a continuation-in-part of Ser. No. 505,030, Apr. 5, 1990, Pat. No. 5,160,528, which is a continuation-in-part of Ser. No. 448,707, Dec. 11, 1989, Pat. No. 5,071,463.

[51] Int. Cl.$^5$ ............... A01N 53/00; A01N 25/00
[52] U.S. Cl. .................. 514/531; 514/772; 514/772.3; 514/788; 514/937; 514/938; 514/970; 514/971
[58] Field of Search ............. 514/970, 971, 937, 938, 514/942, 724, 531, 788, 772, 772.3

[56] References Cited

U.S. PATENT DOCUMENTS

| | | | |
|---|---|---|---|
| 4,870,103 | 9/1989 | Röechling et al. | 514/521 |
| 5,110,591 | 5/1992 | Williams | 424/195.1 |

*Primary Examiner*—Frederick E. Waddell
*Assistant Examiner*—K. Weddington
*Attorney, Agent, or Firm*—Walter Katz; Marilyn J. Maue; Joshua J. Ward

[57] ABSTRACT

A method of stabilizing an aqueous microemulsion of a water-insoluble agriculturally active compound to remain clear and free of precipitation after standing for 6 months at a temperature of 2°-3° C. which comprises adding a polyhydric alcohol with at least 3 hydroxyl groups to the microemulsion.

7 Claims, No Drawings

COLD STABILIZATION OF AQUEOUS MICROEMULSIONS OF A WATER-INSOLUBLE AGRICULTURALLY ACTIVE COMPOUND

CROSS-REFERENCE TO RELATED APPLICATIONS

This application is a continuation-in-part of application Ser. No. 777,032, filed Oct. 16, 1991, now abandoned, which is a continuation-in-part of application Ser. No. 654,250, filed Feb. 12, 1991, now abandoned, which is a continuation-in-part of application Ser. No. 546,014, filed Jun. 28, 1990, Pat. No. 5,165,666, which is a continuation-in-part of application Ser. No. 505,030, filed Apr. 5, 1990 Pat. No. 5,160,528, which is a continuation-in-part of application Ser. No. 448,707, filed Dec. 11, 1989, Pat. No. 5,071,463.

BACKGROUND OF THE INVENTION

A microemulsion is an oil-in-water or water-in-oil, transparent, thermodynamically stable dispersion of two or more immiscible liquids wherein the dispersed phase consists of small droplets with diameters in the range of about 10 to 100 millimicrons. Such microemulsions are known to enhance the efficacy of active compounds relative to equivalent levels of the same compound in a macroemulsion composition. See Skelton, P. R., Munk, B. H., and Collins, H. M., "Formulation of Pesticide Microemulsions", *Pesticide Formulations and Application Systems;* 8th Volume, ASTM STP 980, D. A. Hovde and G. B. Beestman, Eds., American Society for Testing and Materials, Philadelphia, (1988); U.S. Pat. No. 3,954,967; Canadian Patent No. 1,025,687; Prince, L., *Microemulsions, Theory and Practice*, Academic Press, (1977); and "Microemulsions-Properties Novel Chemistry BH Robinson, Chemistry in Britain 26 (1990), page 342.

Aqueous microemulsions of water-insoluble agriculturally active compounds generally exhibit good stability towards precipitation of the active compound at temperatures above about 10° C. However, such compositions usually do not maintain the microemulsion state at temperatures below 10° C., and, particularly, at the low temperatures of 2°-3° C. Ordinarily, such microemulsions become unstable, as evidenced by visible clouding of the otherwise transparent liquid as the temperature is decreased below about 10° C., particularly at 2°-3° C.

DETAILED DESCRIPTION OF THE INVENTION

What is described herein is a method of cold stabilizing an aqueous microemulsion of a water-insoluble agriculturally active ingredient to remain clear and free of precipitation after standing for 6 months at a temperature of about 2°-3° C. which comprises adding a polyhydric alcohol with at least 3 hydroxyl groups to the microemulsion.

The polyhydric alcohol suitably is selected from glycerol, pentaerythritol, mannitol and sorbitol. These polyhydric alcohols are capable of entering the micelles of the microemulsion to hydrogen-bond with any water leaking therein thus precluding precipitation of the active material from the micelle. Glycerol is preferred.

Accordingly, the method of forming stabilized aqueous microemulsion compositions is represented by the formulations given in the Table below, and their physical properties.

TABLE

STABILIZED AQUEOUS MICROEMULSION COMPOSITIONS

| Active Compound | Control | Run No. 1 | Run No. 2 | Run No. 3 |
|---|---|---|---|---|
| Agriculturally | | | | |
| D-Allethrin* | 0.05 | 0.05 | 0.05 | 0.05 |
| Tetramethrin* | 0.20 | 0.20 | 0.20 | 0.15 |
| Permethrin* | 0.15 | 0.15 | 0.15 | 0.20 |
| Piperonyl Butoxide** | 0.9 | 0.9 | 0.9 | 0.9 |
| Lactam | | | | |
| N-methylpyrrolidone | 5.0 | 5.0 | 5.0 | 5.0 |
| N-octylpyrrolidone | 0.625 | 0.625 | 0.625 | 0.625 |
| Surfactant | | | | |
| Igepal CO 630*** | 3.75 | 3.75 | 3.75 | 3.75 |
| Pegol L 31**** | 0.625 | 0.625 | 0.625 | 0.625 |
| Stabilizing Agent | | | | |
| Glycerol | 0 | 2.0 | 5.0 | 10.0 |

*pyrethroids
**a synergist
***nonylphenol ethoxylated alcohol with 9 EOs (ethylene oxide units)
****ethylene oxide (EO)/propylene oxide (PO)/EO block copolymer, 2 EO/16 PO/2 EO-H$_2$O

PHYSICAL PROPERTIES

A. The control formulation showed crystal formation in less than 48 hours at 2°-3° C.

B. The invention formulations of Runs 1-3 were clear and free of precipitation even after standing for 6 months at 2°-3° C.

C. Pentaerythritol, mannitol and sorbitol were substituted for glycerol in Runs 1-3 with similar advantageous results.

COMPARATIVE EXAMPLES

Similar amounts of propylene glycol, butenediol, butanol and isopropanol, i.e. alcohols having less than 3 hydroxyl groups, were substituted for glycerol in the above microemulsion compositions. Clouding or precipitation was observed soon after preparation of these microemulsion compositions, or when stored at 2°-3° C.

While the invention has been described with particular reference to certain embodiments thereof, it will be understood that changes and modifications may be made which are within the skill of the art. Accordingly, it is intended to be bound only by the following claims, in which:

What is claimed is:

1. A method of cold stabilizing an aqueous microemulsion fully diluted with water and ready for use whose micelles consist of droplets with diameters in the range of about 10 to about 100 millimicrons contain a water-insoluble agriculturally active ingredient having a solubility of less than 0.5 g/100 g of water at 25° C., a lactam and a surfactant to remain clear and free of precipitation of said ingredient even after standing for 6 months at a temperature of about 2°-3° C. which comprises adding about 0.5-10% by weight of a polyhydric alcohol with at least 3 hydroxyl groups to the aqueous microemulsion wherein said polyhydric alcohol is capable of entering the micelles of the aqueous microemulsion to hydrogen-bond with any water leaking therein thus precluding undesired precipitation of the agriculturally active ingredient from the micelle.

2. A method according to claim 1 wherein said polyhydric alcohol is glycerol, pentaerythritol, mannitol or sorbitol.

3. A method according to claim 2 wherein said lactam is a mixture of N-octylpyrrolidone and N-methylpyrrolidone.

4. A method according to claim 1 wherein said surfactant is a mixture of a nonylphenol ethoxylated alcohol and an ethylene oxide/propylene oxide block copolymer.

5. A method according to claim 1 wherein said polyhydric alcohol is added in an amount of about 2-5% by weight of said microemulsion.

6. A method according to claim 1 wherein said water-insoluble agriculturally active ingredient is a pyrethroid selected from D-allethrin, tetramethrin and permethrin, and mixtures thereof.

7. A stabilized aqueous microemulsion made according to the method of claim 1.

* * * * *